United States Patent
Kiyomori et al.

(10) Patent No.: US 7,307,178 B2
(45) Date of Patent: Dec. 11, 2007

(54) PROCESSES OF MAKING γ,δ-UNSATURATED CARBOXYLIC ACID AND SILYL ESTER THEREOF, CARBOXYL GROUP-CONTAINING ORGANOSILICON COMPOUND AND PROCESS OF MAKING

(75) Inventors: Ayumu Kiyomori, Niigata-ken (JP); Tohru Kubota, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 392 days.

(21) Appl. No.: 10/947,129

(22) Filed: Sep. 23, 2004

(65) Prior Publication Data

US 2005/0070729 A1    Mar. 31, 2005

(30) Foreign Application Priority Data

Sep. 25, 2003   (JP)   ............. 2003-333014

(51) Int. Cl.
C07F 7/08    (2006.01)

(52) U.S. Cl. .......... 556/443; 556/431; 556/432; 556/440; 556/442; 556/465; 556/466; 556/479; 556/482; 562/598

(58) Field of Classification Search .......... 556/431, 556/432, 440, 442, 479, 482, 443, 465, 466, 556/471; 562/598
See application file for complete search history.

(56) References Cited

U.S. PATENT DOCUMENTS

| 4,734,511 | A | 3/1988 | Inagaki et al. |
| 5,534,562 | A | 7/1996 | Jensen et al. |
| 5,750,753 | A | 5/1998 | Kimae et al. |
| 6,107,504 | A | 8/2000 | Yamamoto et al. |

FOREIGN PATENT DOCUMENTS

| JP | 6-43414 | B2 | 6/1994 |
| JP | 9-202791 | A | 8/1997 |
| JP | 11-193291 | A | 7/1999 |
| JP | 2001-158791 | A | 6/2001 |
| SU | 1397428 | A1 | 5/1988 |

OTHER PUBLICATIONS

Urabe et al., Journal of Organic Chemistry, vol. 49, No. 6, pp. 1140-1141 (1984).*
Qingdao Haiyang Daxue Xuedao, 1999, vol. 29, pp. 319 to 320.
Trost and Fleming Ed., Comprehensive Organic Synthesis, First Edition, Pergamon Press, 1991 pp. 827 to 873.

* cited by examiner

Primary Examiner—Porfirio Nazario-Gonzalez
(74) Attorney, Agent, or Firm—Birch, Stewart, Kolasch & Birch, LLP

(57) ABSTRACT

A γ,δ-unsaturated carboxylic acid silyl ester is prepared by reacting an α,β-unsaturated carboxylic acid ester with a hydrosilane or hydrosiloxane in the presence of tris(pentafluorophenyl)borane. γ,δ-Unsaturated carboxylic acid derivatives are readily prepared through fewer steps and in high yields.

7 Claims, No Drawings

PROCESSES OF MAKING γ,δ-UNSATURATED CARBOXYLIC ACID AND SILYL ESTER THEREOF, CARBOXYL GROUP-CONTAINING ORGANOSILICON COMPOUND AND PROCESS OF MAKING

CROSS-REFERENCE TO RELATED APPLICATION

This non-provisional application claims priority under 35 U.S.C. §119(a) on Patent Application No. 2003-333014 filed in Japan on Sep. 25, 2003, the entire contents of which are hereby incorporated by reference.

TECHNICAL FIELD

This invention relates to processes of preparing γ,δ-unsaturated carboxylic acids and silyl esters thereof which are useful as polymerizable carboxylic acid derivatives and intermediates for the synthesis of pharmaceutical and agricultural chemicals. It also relates to carboxyl group-containing organosilicon compounds which are useful as silane coupling agents or precursors raw materials for the synthesis of modified silicone fluids and siloxane-containing polymers, and processes of preparing the same.

BACKGROUND ART

γ,δ-Unsaturated carboxylic acids have in the molecule two reactive sites, an olefin moiety and a carboxyl group. They are useful as polymerizable monomers in polymer manufacture or as intermediates for the synthesis of pharmaceutical and agricultural chemicals. With respect to 2,2-dimethyl-4-pentenoic acid, for example, U.S. Pat. No. 5,534,562 discloses its use in a primer composition for dental material bonding. Also, JP-B 6-43414 discloses its use as raw material from which pharmaceutical intermediates are prepared.

For preparation of γ,δ-unsaturated carboxylic acids and esters thereof, several processes have been reported, including (a) allylation at α-carbon of carboxylic acids, (b) oxidation of γ,δ-unsaturated aldehydes, and (c) Claisen rearrangement.

Process (a) includes (a-1) where a base acts on a carboxylic acid or ester thereof to generate carbanion at α-position, with which an allylating agent is reacted; (a-2) where a malonic acid ester is reacted with an allylating agent in the presence of a base and a palladium catalyst, followed by decarboxylation; (a-3) where a metal acts on α-halogenated carboxylic acid ester, followed by reaction with an allylating agent; and (a-4) where using a lithium reagent and trialkylchlorosilane, a carboxylic acid ester is converted to a silyl ketene acetal, which is reacted with an allylating agent in the presence of a palladium catalyst. In all these processes, the base or metal must be used in excess of the stoichiometry. This gives rise to drawbacks including a reduced yield per unit reactor volume and the formation of much salt to be discarded.

Qingdao Haiyang Daxue Xuebao, 1999, Vol. 29, pp. 319-320, reports successful results of producing 2,2-dimethyl-4-pentenoic acid in high yields by process (b) using silver oxide as an oxidizing agent. USSR Patent No. 1,397,428 discloses a method of making 2,2-dimethyl-4-pentenoic acid by process (b) using cobalt acetate as a catalyst and molecular oxygen as an oxidizing agent in methanol. However, the synthesis of γ,δ-unsaturated aldehyde used as the starting material is not always satisfactory in yield, cost, reaction time and the like.

By contrast, preparation of γ,δ-unsaturated carboxylic acids and esters thereof by (c) Claisen rearrangement is ideal in that rearrangement reaction per se forms no waste products. See Trost and Fleming Ed., Comprehensive Organic Synthesis, First Edition, Pergamon Press, 1991, pp. 827-873. Problems arise in that ketene acetals used as the starting materials in rearrangement reaction are produced by transesterification (Johnson-Claisen rearrangement) between ortho-ester and allyl alcohol at high temperature, or deprotonation-silylation (Ireland-Claisen rearrangement) of carboxylic acid allyl ester. The former uses a high reaction temperature and lacks selectivity. The latter requires at least one equivalent of the deprotonation agent, from which a large amount of salt is formed. Besides, it was reported to perform Claisen rearrangement by subjecting zinc to act on α-bromocarboxylic acid allyl ester. This method must use an excess amount of zinc powder, undesirably producing a large amount of waste.

JP-A 9-202791 describes that when allyl acrylate is hydrosilylated in the presence of a platinum catalyst, a γ,δ-unsaturated carboxylic acid and silyl ester thereof are formed as by-products through Claisen rearrangement. In this process, formation of γ,δ-unsaturated carboxylic acids takes place as side reaction and only in low yields.

Although γ,δ-unsaturated carboxylic acid derivatives are useful compounds, their preparation process is limited as discussed above. There exists a need for a simple process for their preparation in high yields.

Meanwhile, organosilicon compounds having a carboxyl group are useful as silane coupling agents, precursors raw materials for various modified silicone fluids, and raw materials for polycondensation polymers such as polyamides and polyesters. For their preparation, JP-A 2001-158791 and JP-A 11-193291 disclose methods of preparing siloxanes having carboxylic acid and carboxylic acid ester moieties. In either case, hydrosilylation is utilized to form a silicon-carbon bond. Due to mild reaction, hydrosilylation is effective for the synthesis of silicon compounds having a carboxyl group or precursor thereof. However, there are commercially available few unsaturated carboxylic acids and equivalents to be used as the starting material. Then, the type of carboxyl group-containing organosilicon compounds that can be produced using such starting materials is also limited. It is desired to solve these unsatisfactory problems.

SUMMARY OF THE INVENTION

An object of the present invention is to provide a simple process of preparing γ,δ-unsaturated carboxylic acid derivatives in fewer steps and in high yields. Another object is to provide carboxyl group-containing organosilicon compounds and a process for preparing the same.

The inventors have discovered that by reacting an α,β-unsaturated carboxylic acid ester with a hydrosilane or hydrosiloxane in the presence of a catalytic amount of tris(pentafluorophenyl)borane, a γ,δ-unsaturated carboxylic acid silyl ester can be readily prepared in one step and in high yields, and that by desilylating the resulting silyl ester, a γ,δ-unsaturated carboxylic acid can be prepared in high yields. The inventors have also discovered novel carboxyl group-containing organosilicon compounds and a process for preparing the same.

[I] A process of preparing a γ,δ-unsaturated carboxylic acid silyl ester of the general formula (3), comprising the step of reacting an α,β-unsaturated carboxylic acid ester of the general formula (1) with a hydrosilane or hydrosiloxane of the general formula (2) in the presence of a catalytic amount of tris(pentafluorophenyl)borane.

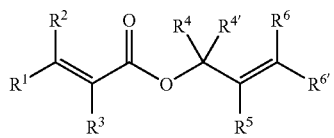
(1)

Herein $R^1$, $R^2$, $R^3$, $R^4$, $R^{4'}$, $R^5$, $R^6$ and $R^{6'}$ are each independently a monovalent $C_1$-$C_{20}$ hydrocarbon group which may be halo-substituted, a halogen atom, or a hydrogen atom, or a pair of $R^1$ and $R^2$, $R^1$ and $R^3$, $R^4$ and $R^{4'}$, $R^4$ and $R^6$, $R^{4'}$ and $R^6$, or $R^5$ and $R^{6'}$ may bond together to form a ring.

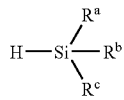
(2)

Herein $R^a$, $R^b$ and $R^c$ are each independently selected from the class consisting of $C_1$-$C_{20}$ alkyl, $C_6$-$C_{20}$ aryl, $C_7$-$C_{20}$ aralkyl, $C_1$-$C_{20}$ alkoxy, $C_6$-$C_{20}$ aryloxy, $C_7$-$C_{20}$ aralkyloxy, organosiloxy groups in which a group bonded to a silicon atom is a monovalent $C_1$-$C_{20}$ hydrocarbon group or hydrogen, substituted forms of the foregoing groups in which a hydrogen atom bonded to a carbon atom is substituted with a halogen atom, and halogen atoms, or a pair of $R^a$ and $R^b$, $R^a$ and $R^c$, or $R^b$ and $R^c$ may bond together to form a siloxane ring of 3 to 50 silicon atoms or a silicon-containing ring of 1 to 20 carbon atoms with the silicon atom to which they are bonded, or $R^a$, $R^b$ and $R^c$ may bond together to form a cage siloxane of 6 to 50 silicon atoms with the silicon atom to which they are bonded.

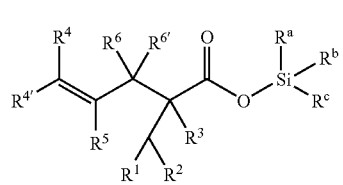
(3)

Herein $R^1$, $R^2$, $R^3$, $R^4$, $R^{4'}$, $R^5$, $R^6$, $R^{6'}$, $R^a$, $R^b$ and $R^c$ a defined in formulae (1) and (2).

[II] A process of preparing a γ,δ-unsaturated carboxylic acid of the general formula (4), comprising the step of desilylating the γ,δ-unsaturated carboxylic acid silyl ester of formula (3) resulting from the process of [I].

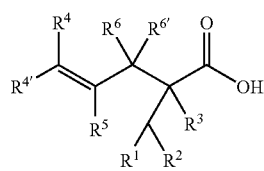
(4)

Herein $R^1$, $R^2$, $R^3$, $R^4$, $R^{4'}$, $R^5$, $R^6$, and $R^{6'}$ are as defined in formula (1).

[III] An organosilicon compound having a silylated carboxyl group, represented by the general formula (5).

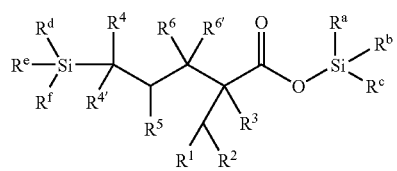
(5)

Herein $R^1$, $R^2$, $R^3$, $R^4$, $R^{4'}$, $R^5$, $R^6$, $R^{6'}$, $R^a$, $R^b$ and $R^c$ are as defined in formulae (1) and (2); Rd is selected from the class consisting of $C_1$-$C_{20}$ alkoxy, $C_6$-$C_{20}$ aryloxy, $C_7$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^e$ and $R^f$ are independently selected from the class consisting of $C_1$-$C_{20}$ alkyl, $C_6$-$C_{20}$ aryl, $C_7$-$C_{20}$ aralkyl, $C_1$-$C_{20}$ alkoxy, $C_6$-$C_{20}$ aryloxy, $C_1$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^d$, $R^e$ and $R^f$ may have a substituent group free of unsaturation that undergoes hydrosilylation, or a pair of $R^d$ and $R^e$, $R^d$ and $R^f$, or $R^e$ and $R^f$ may bond together to form a siloxane ring of 3 to 50 silicon atoms or a silicon-containing ring of 1 to 20 carbon atoms with the silicon atom to which they are bonded, or $R^d$, $R^e$ and $R^f$ may bond together to form a cage siloxane of 6 to 50 silicon atoms with the silicon atom to which they are bonded.

[IV] A process of preparing an organosilicon compound having a silylated carboxyl group represented by the general formula (5), comprising the step of hydrosilylating the γ,δ-unsaturated carboxylic acid silyl ester of formula (3) resulting from the process of [I], using a hydrosilane or hydrosiloxane of the general formula (6).

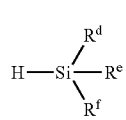
(6)

Herein $R^d$, $R^e$ and $R^f$ are as defined in formula (5).

[V] An organosilicon compound having a carboxyl group, represented by the general formula (7).

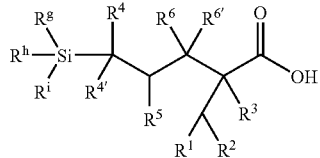

(7)

Herein $R^1$, $R^2$, $R^3$, $R^4$, $R^{4'}$, $R^5$, $R^6$ and $R^{6'}$ are as defined in formulae (1) and (5); $R^g$ is selected from the class consisting of hydroxyl, $C_1$-$C_{20}$ alkoxy, $C_6$-$C_{20}$ aryloxy, $C_7$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^h$ and $R^i$ are independently selected from the class consisting of hydroxyl, $C_1$-$C_{20}$ alkyl, $C_6$-$C_{20}$ aryl, $C_7$-$C_{20}$ aralkyl, $C_1$-$C_{20}$ alkoxy, $C_6$-$C_{20}$ aryloxy, $C_7$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^g$, $R^h$ and $R^i$ may have a substituent group free of unsaturation that undergoes hydrosilylation, or a pair of $R^g$ and $R^h$, $R^g$ and $R^i$, or $R^h$ and $R^i$ may bond together to form a siloxane ring of 3 to 50 silicon atoms or a silicon-containing ring of 1 to 20 carbon atoms with the silicon atom to which they are bonded, or $R^g$, $R^h$ and $R^i$ may bond together to form a cage siloxane of 6 to 50 silicon atoms with the silicon atom to which they are bonded.

[VI] A process of preparing an organosilicon compound having a carboxyl group represented by the general formula (7), comprising the step of desilylating an organosilicon compound having a silylated carboxyl group represented by the general formula (5).

According to the invention, γ,δ-unsaturated carboxylic acid derivatives which are commercially of great interest can be prepared through fewer steps and in high yields. Thereafter, novel organosilicon compounds having a silylated carboxyl group can be prepared therefrom.

DESCRIPTION OF THE PREFERRED EMBODIMENTS

The present invention provides processes of preparing a γ,δ-unsaturated carboxylic acid silyl ester and a γ,δ-unsaturated carboxylic acid. The overall process involves, as shown by the reaction scheme below, the step of reacting an α,β-unsaturated carboxylic acid ester of the general formula (1) with a hydrosilane or hydrosiloxane of the general formula (2) in the presence of a catalytic amount of tris(pentafluorophenyl)borane, to thereby form a γ,δ-unsaturated carboxylic acid silyl ester of the general formula (3); and the step of desilylating the γ,δ-unsaturated carboxylic acid silyl ester of formula (3) to thereby form a γ,δ-unsaturated carboxylic acid of the general formula (4).

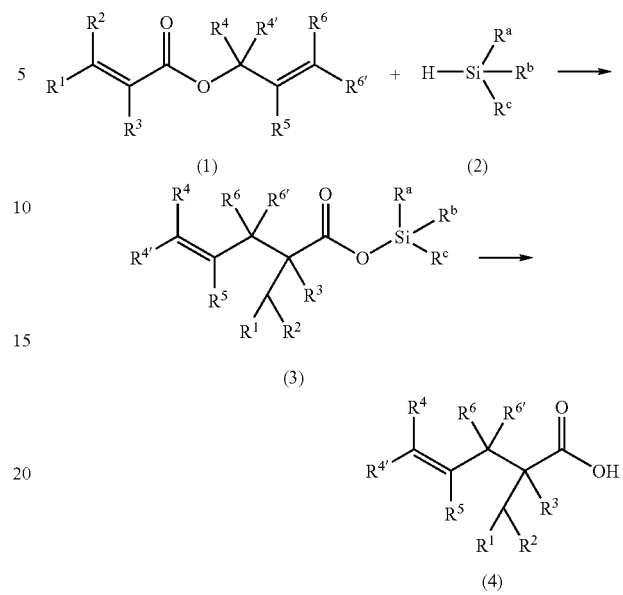

The α,β-unsaturated carboxylic acid ester, with which the inventive process of preparing a γ,δ-unsaturated carboxylic acid and silyl ester thereof starts, has the general formula (1).

Herein $R^1$, $R^2$, $R^3$, $R^4$, $R^{4'}$, $R^5$, $R^6$ and $R^{6'}$ are each independently a monovalent hydrocarbon group of 1 to 20 carbon atoms, preferably 1 to 10 carbon atoms, which may be halo-substituted, a halogen atom, or a hydrogen atom. Alternatively, a pair of $R^1$ and $R^2$, $R^1$ and $R^3$, $R^4$ and $R^{4'}$, $R^4$ and $R^6$, $R^{4'}$ and $R^6$, or $R^5$ and $R^{6'}$ may bond together to form a ring of 3 to 20 carbon atoms, preferably 5 to 10 carbon atoms, with the carbon atom to which they are bonded. Illustrative examples of $R^1$, $R^2$, $R^3$, $R^4$, $R^{4'}$, $R^5$, $R^6$ and $R^{6'}$ include straight, branched or cyclic, unsubstituted or halo-substituted alkyl groups such as methyl, chloromethyl, trifluoromethyl, ethyl, propyl, 3-chloropropyl, isopropyl, butyl, isobutyl, sec-butyl, tert-butyl, pentyl, cyclopentyl, hexyl, cyclohexyl, octyl, decyl, dodecyl and stearyl; straight, branched or cyclic, unsubstituted or halo-substituted alkenyl groups such as vinyl, allyl, 2-propenyl, butenyl, hexenyl, cyclohexenyl, decenyl, and undecenyl; straight, branched or cyclic, unsubstituted or halo-substituted alkynyl groups such as ethynyl, propynyl and butynyl; unsubstituted or halo-substituted aryl groups such as phenyl, 4-fluorophenyl, 4-chlorophenyl, 4-bromophenyl, 4-iodophenyl, pentafluorophenyl, tolyl, xylyl, naphthyl, and biphenylyl; and unsubstituted or halo-substituted aralkyl groups such as benzyl, phenylethyl, and phenylpropyl. Illustrative examples of the ring formed by a pair of R's include cyclopropyl, cyclobutyl, cyclopentyl, cyclohexyl, cyclohexenyl, cyclooctyl, and bicyclo[2.2.1]heptyl rings.

Illustrative examples of the α,β-unsaturated carboxylic acid ester of formula (1) include allyl acrylate, allyl methacrylate, allyl crotonate, allyl cinnamate, methallyl methacrylate and 3-cyclohexenyl methacrylate.

The process of preparing a γ,δ-unsaturated carboxylic acid and silyl ester thereof in a first embodiment of the invention involves reacting an α,β-unsaturated carboxylic acid ester of the general formula (1) with a hydrosilane or hydrosiloxane of the general formula (2).

(2)

Herein $R^a$, $R^b$ and $R^c$ are each independently selected from among alkyl groups of 1 to 20 carbon atoms, preferably 1 to 18 carbon atoms, aryl groups of 6 to 20 carbon atoms, preferably 6 to 12 carbon atoms, aralkyl groups of 7 to 20 carbon atoms, preferably 7 to 14 carbon atoms, alkoxy groups of 1 to 20 carbon atoms, preferably 1 to 10 carbon atoms, aryloxy groups of 6 to 20 carbon atoms, preferably 6 to 12 carbon atoms, aralkyloxy groups of 7 to 20 carbon atoms, preferably 7 to 14 carbon atoms, organosiloxy groups of 1 to 1,000 silicon atoms, preferably 1 to 200 silicon atoms in which a group bonded to a silicon atom is a monovalent hydrocarbon group of 1 to 20 carbon atoms, preferably 1 to 18 carbon atoms (e.g., alkyl or aryl) or hydrogen, substituted forms of the foregoing groups in which a hydrogen atom bonded to a carbon atom is substituted with a halogen atom, and halogen atoms. Alternatively, a pair of $R^a$ and $R^b$, $R^a$ and $R^c$, or $R^b$ and $R^c$ may bond together to form a siloxane ring of 3 to 50 silicon atoms, preferably 3 to 20 silicon atoms or a silicon-containing ring of 1 to 20 carbon atoms with the silicon atom to which they are bonded, or $R^a$, $R^b$ and $R^c$ may bond together to form a cage siloxane of 6 to 50 silicon atoms, preferably 6 to 20 silicon atoms with the silicon atom to which they are bonded.

Illustrative examples of $R^a$, $R^b$ and $R^c$ include straight, branched or cyclic, unsubstituted or halo-substituted alkyl groups such as methyl, chloromethyl, trifluoromethyl, ethyl, propyl, 3-chloropropyl, 3,3,3-trifluoropropyl, isopropyl, butyl, isobutyl, sec-butyl, tert-butyl, pentyl, cyclopentyl, hexyl, cyclohexyl, octyl, decyl, dodecyl and stearyl; unsubstituted or halo-substituted aryl groups such as phenyl, 4-fluorophenyl, 4-chlorophenyl, 4-bromophenyl, 4-iodophenyl, pentafluorophenyl, tolyl, xylyl, naphthyl, and biphenylyl; unsubstituted or halo-substituted aralkyl groups such as benzyl, phenylethyl, and phenylpropyl; unsubstituted or halo-substituted alkoxy groups such as methoxy, ethoxy, propoxy, isopropoxy, butoxy, sec-butoxy, tert-butoxy, isobutoxy, cyclopentyloxy, cyclohexyloxy, and norbornyloxy; unsubstituted or halo-substituted aryloxy groups such as phenoxy, 3-chlorophenoxy, and naphthyloxy; unsubstituted or halo-substituted aralkyloxy groups such as benzyloxy, 2-chlorobenzyloxy, 3-chlorobenzyloxy, 4-chlorobenzyloxy, and naphthylethyloxy; and straight, branched or cyclic (poly)organosiloxy groups of 1 to 1,000 silicon atoms, preferably 1 to 200 silicon atoms, such as dimethylsiloxy, diethylsiloxy, diphenylsiloxy, trimethylsiloxy, chloromethyldimethylsiloxy, triethylsiloxy, phenyldimethylsiloxy, diphenylmethylsiloxy, 1,1,3,3,3-pentamethyldisiloxanyloxy, 1,1,3,3-tetramethyldisiloxanyloxy, ω-methylpolydimethylsiloxanyloxy, ω-hydropolydimethylsiloxanyloxy, polyhydromethylsiloxanyloxy, methylbis(trimethylsiloxy)siloxy, methylbis(dimethylsiloxy)siloxy, tris(trimethylsiloxy)siloxy, 1,3,3,5,5-pentamethylcyclotrisiloxan-1-yloxy, 1,3,5-trimethyl-3,5-bis(3,3,3-trifluoropropyl)cyclo-trisiloxan-1-yloxy, and 1,3,5,7-tetramethylcyclotetrasiloxan-1-yloxy.

Illustrative, non-limiting examples of the cage siloxane are given below.

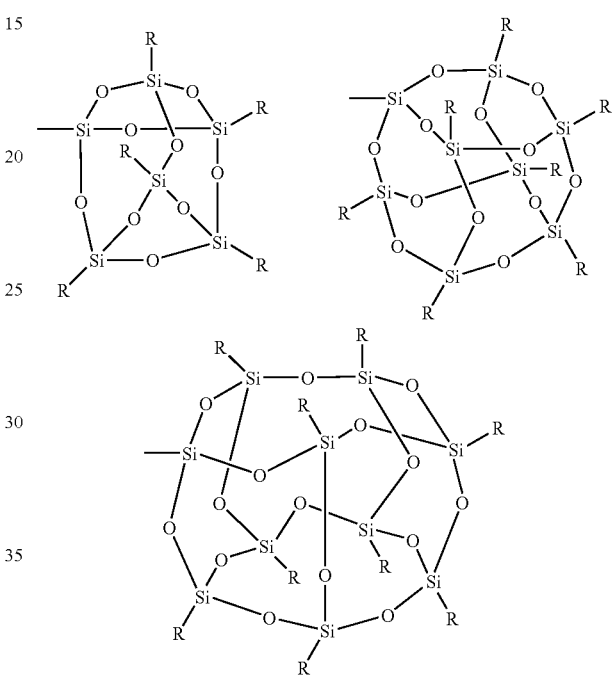

Illustrative, non-limiting examples of the compound of formula (2) include trimethylsilane, chloromethyldimethylsilane, ethyldimethylsilane, 3-chloropropyldimethylsilane, 3,3,3-trifluoropropyldimethylsilane, diethylmethylsilane, triethylsilane, tripropylsilane, triisopropylsilane, tributylsilane, triisobutylsilane, tert-butyldimethylsilane, hexyldimethylsilane, cyclohexyldimethylsilane, thexyldimethylsilane, thexyldiisopropylsilane, decyldimethylsilane, octadecyldimethylsilane, benzyldimethylsilane, dimethylphenylsilane, methyldiphenylsilane, triphenylsilane, tri-p-tolylsilane, tri-o-tolylsilane, methoxydimethylsilane, dimethoxymethylsilane, trimethoxysilane, ethyldimethoxysilane, propyldimethoxysilane, ethoxydimethylsilane, diethoxymethylsilane, triethoxysilane, isopropoxydimethylsilane, sec-butoxydimethylsilane, tert-butoxydimethylsilane, dimethylphenoxysilane, benzyloxydimethylsilane, chlorodimethylsilane, dichloromethylsilane, trichlorosilane, chlorodiethylsilane, dichloroethylsilane, chlorodiphenylsilane, dichlorophenylsilane, pentamethyldisiloxane, 3-chloropropyl-1,1,3,3-tetramethyldisiloxane, 1,1,3,3,5,5,5-heptamethyltrisiloxane, 1,1,3,3-tetramethyldisiloxane, 1,1,3,3-tetraisopropyldisiloxane, 1,3-dimethyl-1,3-diphenyldisiloxane, 1,1,3,3,5,5-hexamethyltrisiloxane, 1,1,1,3,5,5,5-heptamethyltrisiloxane, 1,1,1,3,5,7,7,7- octamethyltetrasiloxane, 1,3,5,7-tetramethylcyclotetrasiloxane, tris(trimethylsiloxy)silane, 1-hydrido-3,5,7,9,11,13,15-heptacyclopentylpentacyclo-[9.5.1.1$^{3,9}$.1$^{5,15}$.1$^{7,13}$]octasiloxane, 1-[hydridodimethylsiloxy]-3,5,7,9,11,13,15-heptacyclopentyl-pentacyclo [9.5.1.1$^{3,9}$.1$^{5,15}$.1$^{7,13}$]octasiloxane, 1,3,5,7,9,11,13,15-octakis(dimethylsiloxy)pentacyclo-[9.5.1.1$^{3,9}$.1$^{5,15}$.1$^{7,13}$] octasiloxane, α-hydro-ω-methylpolydimethylsiloxane, α,ω-dihydropolydimethylsiloxane, and polymethylhydrosiloxane.

In the reaction, the compound of formula (2) is preferably used in such amounts to provide 0.5 to 1.5 moles, more preferably 0.9 to 1.1 moles of Si—H bond per mole of the compound of formula (1). Less amounts of the compound of formula (2) may reduce the yield based on the compound of formula (1). If the compound of formula (2) is used in large excess, side reactions may precede, leading to lower yields.

In the process for preparing γ,δ-unsaturated carboxylic acid and silyl ester thereof according to the first embodiment of the invention, the compound of formula (1) is reacted with the compound of formula (2) in the presence of a catalytic amount, specifically 0.0001 to 10 mol % of tris(pentafluorophenyl)borane. The reaction is typically performed under atmospheric pressure and in an inert gas atmosphere. The reaction temperature is typically from −100° C. to 150° C., preferably from −78° C. to 100° C. At lower temperatures, the reaction may proceed slowly, inducing more side reactions. Higher temperatures may promote deactivation of the catalyst.

Any desired technique may be used to mix the reactants and catalyst. In order for the reaction to proceed under controlled conditions, preferably either one or both of the compounds of formulae (1) and (2) are continuously fed to the reactor charged with the catalyst during the progress of reaction. The reaction solvent is not always necessary. Solventless reaction takes place when both the reactants (1) and (2) are liquid. A solvent may be used to help effective reaction. Suitable solvents include hydrocarbon solvents such as hexane, isooctane, benzene, toluene and xylene and halogenated hydrocarbon solvents such as dichloromethane and dichloroethane.

In the course of reaction, a polymerization inhibitor may be optionally added. If used, the polymerization inhibitor is preferably selected from hindered phenol polymerization inhibitors such as 2,6-di-tert-butyl-4-methylphenol (BHT).

The inventive process is successful in producing a γ,δ-unsaturated carboxylic acid silyl ester of the general formula (3) in one step.

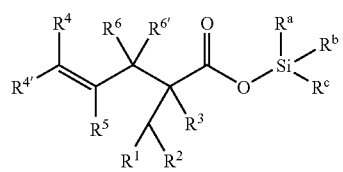

(3)

In formula (3), R$^1$, R$^2$, R$^3$, R$^4$, R$^{4'}$, R$^5$, R$^6$, and R$^{6'}$ are as defined in formula (1), and R$^a$, R$^b$ and R$^c$ are as defined in formula (2).

By desilylating the γ,δ-unsaturated carboxylic acid silyl ester of formula (3) resulting from the above process, a γ,δ-unsaturated carboxylic acid of the general formula (4) can be prepared.

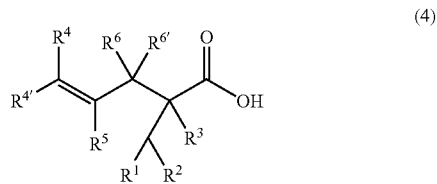

(4)

In formula (4), R$^1$, R$^2$, R$^3$, R$^4$, R$^{4'}$, R$^5$, R$^6$, and R$^{6'}$ are as defined in formula (1).

The desilylation to form the compound of formula (4) is typically hydrolysis or alcoholysis. The alcohol used in the alcoholysis is typically methanol or ethanol. The alcohol may be used in any desired amount of at least one equivalent per mole of the compound of formula (3), typically 1 to 10 equivalents per mole of the compound of formula (3). The reaction temperature is typically from −20° C. to 150° C., preferably from 0° C. to 100° C. Hydrolysis or alcoholysis is often carried out in the presence of an acid such as acetic acid, hydrochloric acid, or trifluoroacetic acid, a base such as sodium hydroxide, sodium carbonate, potassium carbonate, sodium methoxide or sodium ethoxide, or a fluoride such as tetrabutylammonium fluoride, so as to accelerate the reaction. When the reaction is carried out in the presence of a base, the reaction solution at the end of reaction must be adjusted to be acidic so that the compound of formula (4) is liberated. Desilylation reaction can be carried out after the silyl ester of formula (3) is isolated. Alternatively, after the silyl ester of formula (3) is synthesized from the compounds of formulae (1) and (2) by the inventive process, the reaction mixture is subjected to desilylation reaction, and the compound of formula (4) is finally isolated and purified.

A further embodiment of the invention is a novel organosilicon compound having a silylated carboxyl group, represented by the general formula (5).

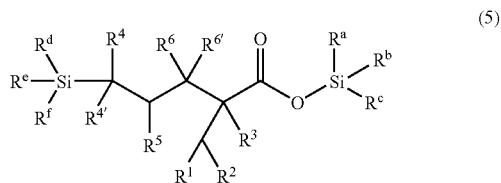

(5)

In formula (5), R$^1$, R$^2$ R$^3$ R$^4$, R$^{4'}$, R$^5$, R$^6$, R$^{6'}$, R$^a$, R$^b$ and R$^c$ are as defined in formulae (1) and (2).

R$^d$ is selected from among alkoxy groups of 1 to 20 carbon atoms, preferably 1 to 10 carbon atoms, aryloxy groups of 6 to 20 carbon atoms, preferably 6 to 12 carbon atoms, aralkyloxy groups of 7 to 20 carbon atoms, preferably 7 to 14 carbon atoms, organosiloxy groups of 1 to 1,000 silicon atoms, preferably 1 to 200 silicon atoms in which a group bonded to a silicon atom is a substituted or unsubstituted monovalent hydrocarbon group of 1 to 20 carbon atoms, preferably 1 to 18 carbon atoms or hydrogen, and halogen atoms. $R^e$ and $R^f$ are independently selected from among alkyl groups of 1 to 20 carbon atoms, preferably 1 to 18 carbon atoms, aryl groups of 6 to 20 carbon atoms, preferably 6 to 12 carbon atoms, aralkyl groups of 7 to 20 carbon atoms, preferably 7 to 14 carbon atoms, alkoxy groups of 1 to 20 carbon atoms, preferably 1 to 10 carbon atoms, aryloxy groups of 6 to 20 carbon atoms, preferably 6 to 12 carbon atoms, aralkyloxy groups of 7 to 20 carbon atoms, preferably 7 to 14 carbon atoms, organosiloxy groups of 1 to 1,000 silicon atoms, preferably 1 to 200 silicon atoms in which a group bonded to a silicon atom is a substituted or unsubstituted monovalent hydrocarbon group of 1 to 20 carbon atoms, preferably 1 to 18 carbon atoms or hydrogen, and halogen atoms. $R^d$, $R^e$ and $R^f$ may have a substituent group free of unsaturation that undergoes hydrosilylation. Alternatively, a pair of $R^d$ and $R^e$, $R^d$ and $R^f$, or $R^e$ and $R^f$ may bond together to form a siloxane ring of 3 to 50 silicon atoms, preferably 3 to 20 silicon atoms or a silicon-containing ring of 1 to 20 carbon atoms with the silicon atom to which they are bonded, or $R^d$, $R^e$ and $R^f$ may bond together to form a cage siloxane of 6 to 50 silicon atoms, preferably 6 to 20 silicon atoms with the silicon atom to which they are bonded.

Preferred are those compounds of formula (5) wherein $R^1$, $R^2$, $R^4$, $R^{4'}$, $R^5$, $R^6$, and $R^{6'}$ are hydrogen and $R^3$ is methyl. Examples of the substituted or unsubstituted monovalent hydrocarbon group bonded to a silicon atom include alkyl groups, aryl groups, and substituted forms of these groups in which some or all hydrogen atoms are substituted with halogen atoms, hydroxyl groups, carboxyl groups, or triorganosiloxycarbonyl groups such as trialkylsiloxycarbonyl.

The groups represented by $R^d$, $R^e$ and $R^f$ may have thereon substituent groups free of an unsaturated bond in which a hydrogen atom bonded to a carbon atom is that undergoes hydrosilylation (especially with the aid of platinum catalyst), for example, halogen atoms, alkoxy groups of 1 to 20 carbon atoms, preferably 1 to 10 carbon atoms, aryloxy groups of 6 to 20 carbon atoms, preferably 6 to 12 carbon atoms, and acyloxy groups of 1 to 20 carbon atoms, preferably 2 to 10 carbon atoms.

Illustrative examples of $R^d$ include unsubstituted or substituted alkoxy groups such as methoxy, ethoxy, propoxy, isopropoxy, butoxy, sec-butoxy, tert-butoxy, isobutoxy, cyclopentyloxy, cyclohexyloxy, norbornyloxy, methoxyethoxy, and acetoxyethoxy; unsubstituted or substituted aryloxy groups such as phenoxy, 4-fluorophenoxy, 4-chlorophenoxy, 4-methoxyphenoxy, and naphthyloxy; unsubstituted or substituted aralkyloxy groups such as benzyloxy, 2-chlorobenzyloxy, 3-chlorobenzyloxy, and naphthylethyloxy; and straight, branched or cyclic (poly)organosiloxy groups of 1 to 1,000 silicon atoms, preferably 1 to 200 silicon atoms, such as dimethylsiloxy, diethylsiloxy, diphenylsiloxy, trimethylsiloxy, chloromethyldimethylsiloxy, (2-trimethylsiloxycarbonylethyl)dimethylsiloxy, (2-triethylsiloxycarbonylethyl)dimethylsiloxy, (4-triethylsiloxycarbonyl-4-methylpentyl)dimethylsiloxy, triethylsiloxy, phenyldimethylsiloxy, diphenylmethylsiloxy, 1,1,3,3,3-pentamethyldisiloxanyloxy, 1,1,3,3-tetramethyldisiloxanyloxy, 3-(4-triethylsiloxycarbonyl-4-methylpentyl)-1,1,3,3-tetramethyldisiloxanyloxy, ω-methylpolydimethylsiloxanyloxy, ω-hydropolydimethyl-siloxanyloxy, ω-(4-triethylsiloxycarbonyl-4-methylpentyl)-polydimethylsiloxanyloxy, polyhydromethylsiloxanyloxy, methylbis(trimethylsiloxy)siloxy, methylbis(dimethylsiloxy)siloxy, tris(trimethylsiloxy)siloxy, 1,3,3,5,5-pentamethylcyclotrisiloxan-1-yloxy, 1,3,5-trimethyl-3,5-bis(3,3,3-trifluoropropyl)-cyclotrisiloxan-1-yloxy, and 1,3,5,7-tetramethylcyclotetrasiloxan-1-yloxy. Examples of $R^e$ and $R^f$ include those exemplified above for $R^d$, and straight, branched or cyclic, substituted or unsubstituted alkyl groups such as methyl, chloromethyl, ethyl, methoxyethyl, propyl, 3-chloropropyl, 3,3,3-trifluoropropyl, isopropyl, butyl, isobutyl, sec-butyl, tert-butyl, pentyl, cyclopentyl, hexyl, cyclohexyl, octyl, decyl, dodecyl, and stearyl; substituted or unsubstituted aryl groups such as phenyl, p-chlorophenyl, tolyl, p-methoxyphenyl, p-fluorophenyl, pentafluorophenyl, naphthyl, and biphenyl; and substituted or unsubstituted aralkyl groups such as benzyl, p-methoxybenzyl, p-bromobenzyl, phenylethyl and phenylpropyl.

Illustrative, non-limiting examples of the cage siloxane are given below.

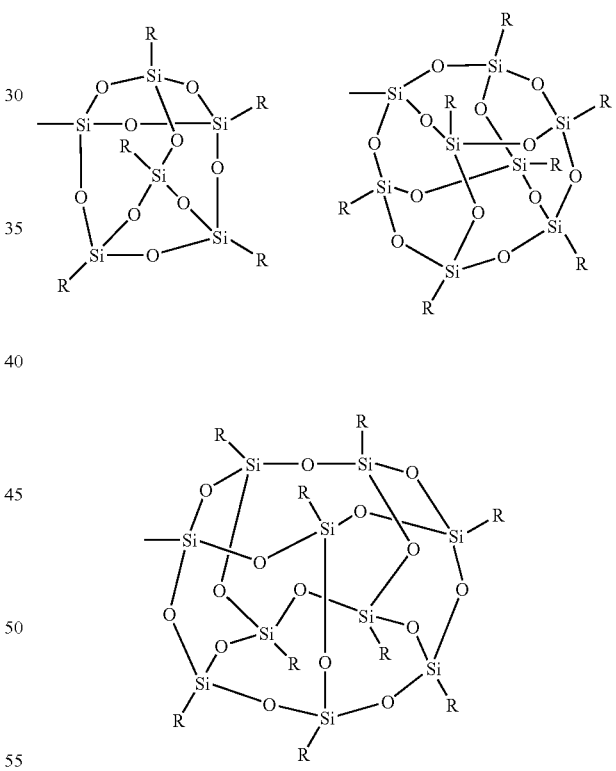

A still further embodiment of the invention is a process of preparing the compound of formula (5). The process of preparing an organosilicon compound having a silylated carboxyl group represented by formula (5) comprises the step of hydrosilylating the γ,δ-unsaturated carboxylic acid silyl ester of formula (3) resulting from the process of the first embodiment, using a hydrosilane or hydrosiloxane of the general formula (6), as shown below by the reaction scheme.

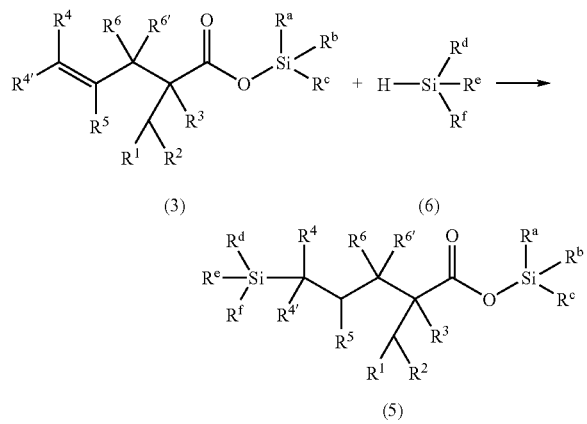

(3)  (6)

(5)

In formula (6), $R^d$, $R^e$ and $R^f$ are as defined in formula (5). Illustrative examples of the compound of formula (6) include methoxydimethylsilane, dimethoxymethylsilane, trimethoxysilane, ethyldimethoxysilane, propyldimethoxysilane, ethoxydimethylsilane, diethoxymethylsilane, triethoxysilane, isopropoxydimethylsilane, sec-butoxydimethylsilane, tert-butoxydimethylsilane, (2-methoxyethoxy)dimethylsilane, [2-(2-methoxyethoxy)ethoxy]dimethylsilane, dimethylphenoxysilane, (4-chlorophenoxy)dimethylsilane, benzyloxydimethylsilane, chlorodimethylsilane, dichloromethylsilane, trichlorosilane, chlorodiethylsilane, dichloroethylsilane, chlorodiphenylsilane, dichlorophenylsilane, (4-chlorophenyl)dichlorosilane, pentamethyldisiloxane, 3-chloropropyl-1,1,3,3-tetramethyldisiloxane, 1,1,3,3,5,5,5-heptamethyltrisiloxane, 1,1,3,3-tetramethyldisiloxane, 1,1,3,3-tetraisopropyldisiloxane, 1,3-dimethyl-1,3-diphenyldisiloxane, 1,1,3,3,5,5-hexamethyltrisiloxane, 1,1,1,3,5,5,5-heptamethyltrisiloxane, 1,1,1,3,5,7,7,7-octamethyltetrasiloxane, 1,3,5,7-tetramethylcyclotetrasiloxane, tris(trimethylsiloxy)silane, 1-hydrido-3,5,7,9,11,13,15-heptacyclopentylpentacyclo-[9.5.1.1$^{3,9}$.1$^{5,15}$.1$^{7,13}$]octasiloxane, 1-[hydridodimethylsiloxy]-3,5,7,9,11,13,15-heptacyclopentyl-pentacyclo [9.5.1.1$^{3,9}$.1$^{5,15}$.1$^{7,13}$]octasiloxane, 1,3,5,7,9,11,13,15-octakis(dimethylsiloxy)pentacyclo-[9.5.1.1$^{3,9}$.1$^{5,15}$.1$^{7,13}$]octasiloxane, α-hydro-ω-methylpolydimethylsiloxane, α,ω-dihydropolydimethylsiloxane, and polymethylhydrosiloxane.

In the process of preparing an organosilicon compound of formula (5), the γ,δ-unsaturated carboxylic acid silyl ester of formula (3) is hydrosilylated using a hydrosilane or hydrosiloxane of formula (6). The hydrosilylation reaction is performed preferably in the presence of a catalyst. Suitable hydrosilylation catalysts include salts and complexes of Group 8 to 10 transition metals such as ruthenium, rhodium, palladium, iridium and platinum, and such transition metals on carriers. Inter alia, platinum catalysts, especially platinum compounds are preferred. Suitable platinum catalysts include chloroplatinic acid, platinum(0) tetramethyldivinyldisiloxane complex, platinum(0) tetramethyltetravinylcyclotetrasiloxane complex, platinum oxide, and platinum on activated carbon.

The hydrosilylation reaction may be performed in a solventless system, and the use of solvent is optional. If used, suitable solvents include hydrocarbon solvents such as hexane, isooctane, toluene and xylene, and ether solvents such as diethyl ether and tetrahydrofuran. The temperature for hydrosilylation reaction is typically from 0° C. to 200° C., preferably from 20° C. to 100° C. The hydrosilylation reaction is performed preferably in an inert atmosphere, although dry air or oxygen may be fed during the reaction, if necessary. The reactants may be fed in any of various charge modes. In one exemplary mode, the compound of formula (6) is fed to a mixture of the compound of formula (3), the catalyst and an optional solvent. In another mode, the compound of formula (3) is fed to a mixture of the compound of formula (6), the catalyst and an optional solvent.

The compound of formula (3) may be used in isolated form. For simplicity, however, after the compound of formula (3) is produced in a crude mixture form by the process of the first embodiment, hydrosilylation can be performed by adding a hydrosilylation catalyst to the crude mixture and combining the crude mixture with the compound of formula (6).

Still further embodiments of the invention are a novel carboxyl group-containing organosilicon compound having the general formula (7) and a process for preparing the same.

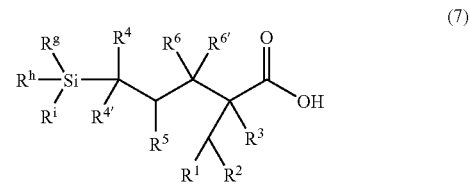

(7)

In formula (7), $R^1$, $R^2$, $R^3$, $R^4$, $R^{4'}$, $R^5$, $R^6$ and $R^{6'}$ are as defined in formulae (1) and (5).

$R^g$ is selected from among hydroxyl, alkoxy groups of 1 to 20 carbon atoms, preferably 1 to 10 carbon atoms, aryloxy groups of 6 to 20 carbon atoms, preferably 6 to 12 carbon atoms, aralkyloxy groups of 7 to 20 carbon atoms, preferably 7 to 14 carbon atoms, organosiloxy groups of 1 to 1,000 silicon atoms, preferably 1 to 200 silicon atoms in which a group bonded to a silicon atom is a substituted or unsubstituted monovalent hydrocarbon group of 1 to 20 carbon atoms, preferably 1 to 18 carbon atoms or hydrogen, and halogen atoms. $R^h$ and $R^i$ are independently selected from among hydroxyl, alkyl groups of 1 to 20 carbon atoms, preferably 1 to 18 carbon atoms, aryl groups of 6 to 20 carbon atoms, preferably 6 to 12 carbon atoms, aralkyl groups of 7 to 20 carbon atoms, preferably 7 to 14 carbon atoms, alkoxy groups of 1 to 20 carbon atoms, preferably 1 to 10 carbon atoms, aryloxy groups of 6 to 20 carbon atoms, preferably 6 to 12 carbon atoms, aralkyloxy groups of 7 to 20 carbon atoms, preferably 7 to 14 carbon atoms, organosiloxy groups of 1 to 1,000 silicon atoms, preferably 1 to 200 silicon atoms in which a group bonded to a silicon atom is a substituted or unsubstituted monovalent hydrocarbon group of 1 to 20 carbon atoms, preferably 1 to 18 carbon atoms or hydrogen, and halogen atoms. Examples of the substituted or unsubstituted monovalent hydrocarbon group bonded to a silicon atom include alkyl groups, aryl groups, and substituted forms of these groups in which some or all hydrogen atoms are substituted with halogen atoms, hydroxyl groups, carboxyl groups, or triorganosiloxycarbonyl groups such as trialkylsiloxycarbonyl. $R^g$, $R^h$ and $R^i$ may have a substituent group free of unsaturation that undergoes hydrosilylation (especially with the aid of platinum catalyst). Alternatively, a pair of $R^g$ and $R^h$, $R^g$ and $R^i$, or $R^h$ and $R^i$ may bond together to form a siloxane ring of 3 to 50 silicon atoms, preferably 3 to 20 silicon atoms or a silicon-containing ring of 1 to 20 carbon atoms with the silicon atom to which they are bonded, or $R^g$, $R^h$ and $R^i$ may bond together to form a cage siloxane of 6 to 50 silicon atoms, preferably 6 to 20 silicon atoms with the silicon atom to which they are bonded.

Illustrative examples of $R^g$ include unsubstituted or substituted alkoxy groups such as methoxy, ethoxy, propoxy, isopropoxy, butoxy, sec-butoxy, tert-butoxy, isobutoxy, cyclopentyloxy, cyclohexyloxy, norbornyloxy, methoxyethoxy, and acetoxyethoxy; unsubstituted or substituted aryloxy groups such as phenoxy, 4-fluorophenoxy, 4-chlorophenoxy, 4-methoxyphenoxy, and naphthyloxy; unsubstituted or substituted aralkyloxy groups such as benzyloxy, 2-chlorobenzyloxy, 3-chlorobenzyloxy, and naphthylethyloxy; and straight, branched or cyclic (poly)organosiloxy groups of 1 to 1,000 silicon atoms, preferably 1 to 200 silicon atoms, such as dimethylsiloxy, diethylsiloxy, diphenylsiloxy, trimethylsiloxy, chloromethyldimethylsiloxy, (2-trimethylsiloxycarbonylethyl)dimethylsiloxy, (2-triethylsiloxycarbonylethyl)dimethylsiloxy, (4-triethylsiloxycarbonyl-4-methylpentyl)dimethylsiloxy, triethylsiloxy, phenyldimethylsiloxy, diphenylmethylsiloxy, 1,1,3,3,3-pentamethyldisiloxanyloxy, 1,1,3,3-tetramethyldisiloxanyloxy, 3-(4-triethylsiloxycarbonyl-4-methylpentyl)-1,1,3,3-tetramethyldisiloxanyloxy, ω-methylpolydimethylsiloxanyloxy, ω-hydropolydimethylsiloxanyloxy, ω-(4-triethylsiloxycarbonyl-4-methylpentyl)polydimethyl-siloxanyloxy, (4-carboxy-4-methylpentyl)dimethylsiloxy, 3-(4-carboxy-4-methylpentyl)-1,1,3,3-tetramethyldisiloxanyloxy, and ω-(4-carboxy-4-methylpentyl)polydimethylsiloxanyloxy. Examples of $R^h$ and $R^i$, other than hydroxyl, include those exemplified above for $R^e$ and $R^f$.

The organosilicon compound having a carboxyl group represented by formula (7) can be prepared by desilylating the organosilicon compound having a silylated carboxyl group represented by formula (5). Like the desilylation reaction of the compound of formula (3), this desilylation reaction may be performed, for example, by hydrolysis or alcoholysis.

Where any one or all of Si—$R^d$ bond, Si—$R^e$ bond and Si—$R^f$ bond are hydrolyzable, there is a possibility that hydrolysis of these bonds takes place to form a silanol at the same time as the desilylation reaction, which silanol is further condensed to form a siloxane bond.

EXAMPLE

Examples of the invention are given below by way of illustration and not by way of limitation. All reactions were performed in a nitrogen atmosphere.

Example 1

Synthesis of triethylsilyl 2,2-dimethyl-4-pentenoate by Reaction of Allyl Methacrylate with Triethylsilane A 300-ml four-necked flask equipped with a Dimroth reflux condenser, stirrer, thermometer and dropping funnel was purged with nitrogen. The flask was charged with 25.6 mg (0.050 mmol) of tris(pentafluorophenyl)borane (by Aldrich, lot No. 18609AO, same hereinafter), 1.29 g of 1,3,5-tris(3,5-di-tert-butyl-4-hydroxybenzyl)-2,4,6-trimethylbenzene (Irganox 1330, Ciba Specialty Chemicals), and 58.2 g (0.50 mol) of triethylsilane, which were stirred at room temperature for 0.5 hour. The flask was heated in an oil bath to an internal temperature of 40° C., after which 37.9 g (0.30 mol) of allyl methacrylate was added dropwise over 2 hours from the dropping funnel. Since exothermic heat was observed during the dropwise addition, the oil bath heating was adjusted so as to maintain an internal temperature of 40-50° C. A 10% toluene solution of 12.8 mg (0.025 mmol) tris(pentafluorophenyl)borane was added, after which 25.2 g (0.20 mol) of allyl methacrylate was added dropwise at 40-50° C. over 1.2 hours from the dropping funnel. After 5 minutes from the end of dropwise addition, the disappearance of triethylsilane was confirmed by gas chromatography. The reaction solution which was colorless and clear was vacuum distilled, collecting 115.9 g of a colorless clear liquid having a boiling point of 74.5-76.5° C./0.3 kPa. On analysis by NMR spectroscopy and GC/MS spectroscopy, the liquid was identified to be the target compound, triethylsilyl 2,2-dimethyl-4-pentenoate. The yield was 95.6%.

$^1$H-NMR (CDCl$_3$, 300 MHz): δ (ppm) 5.81-5.67 (1H, m), 5.07-5.04 (1H, m), 5.03-5.00 (1H, m), 2.26 (2H, dt, J=7.4 Hz, 1.2 Hz), 1.15 (6H, s), 0.97 (9H, t, J=7.8 Hz), 0.75 (6H, q, J=7.8 Hz) $^{13}$C-NMR (CDCl$_3$, 75.6 MHz): δ (ppm) 178.0, 134.4, 117.7, 44.7, 43.2, 24.9, 6.5, 4.5 MS (EI): m/z 242 (M+), 213, 172, 115, 87, 75

Example 2

Synthesis of ethoxydimethylsilyl 2,2-dimethyl-4-pentenoate by Reaction of Allyl Methacrylate with Ethoxydimethylsilane A 100-ml four-necked flask equipped with a Dimroth reflux condenser, stirrer, thermometer and dropping funnel was purged with nitrogen. The flask was charged with 220 mg of BHT, 5 ml of toluene, and a 10% toluene solution of 2.6 mg (0.005 mmol) tris(pentafluorophenyl)borane. While the contents were stirred, the flask was cooled at 4° C. in an ice water bath. A mixture of 12.6 g (0.10 mol) of allyl methacrylate and 10.4 g (0.10 mol) of ethoxydimethylsilane was added dropwise over 3.5 hours from the dropping funnel. The internal temperature rose to 12° C. at maximum.

After the completion of dropwise addition, the contents were stirred at 4° C. for a further 2 hours. Then 7 µl (0.05 mmol) of triethylamine was added to the reaction mixture, which was vacuum distilled, collecting 19.7 g of a colorless clear fraction having a boiling point of 61-62° C./0.7 kPa. On NMR and GC/MS analysis, the liquid was identified to be the target compound, ethoxydimethylsilyl 2,2-dimethyl-4-pentenoate. The yield was 85.5%.

$^1$H-NMR (CDCl$_3$, 300 MHz): δ (ppm) 5.81-5.67 (1H, m), 5.09-5.05 (1H, m), 5.05-5.01 (1H, m), 3.83 (2H, q, J=7.0 Hz), 2.26 (2H, dt, J=7.4 Hz, 1.1 Hz), 1.21 (3H, t, J=7.0 Hz), 1.16 (6H, s), 0.28 (6H, s) $^{13}$C-NMR (CDCl$_3$, 75.6 MHz): δ (ppm) 177.5, 134.2, 117.8, 59.1, 44.7, 43.1, 24.7, 18.2, −2.4 MS (EI): m/z 230 (M$^+$), 215, 185, 184, 174, 103, 75

Example 3

Synthesis of Chlorodimethylsilyl 2,2-dimethyl-4-pentenoate by Reaction of Allyl Methacrylate with Chlorodimethylsilane A 100-ml four-necked flask equipped with a Dimroth reflux condenser, stirrer, thermometer and dropping funnel was purged with nitrogen. The flask was charged with 220 mg of BHT, 5 ml of toluene, and 51 mg (0.10 mmol) of tris(pentafluorophenyl)borane. While the contents were stirred, the flask was cooled at 2.5° C. in an ice water bath. A mixture of 12.6 g (0.10 mol) of allyl methacrylate and 9.5 g (0.10 mol) of chlorodimethylsilane was added dropwise over 3.5 hours from the dropping funnel. The internal temperature rose to 12° C. at maximum. After the completion of dropwise addition, the contents were stirred at 2° C. for a further 2 hours. The pale yellow reaction mixture was vacuum distilled, collecting 16.1 g of a colorless clear fraction having a boiling point of 70-70.5° C./1.2 kPa. On NMR and GC/MS analysis, the liquid was identified to be the target compound, chlorodimethylsilyl 2,2-dimethyl-4-pentenoate. The yield was 72.9%.

$^1$H-NMR (CDCl$_3$, 300 MHz): δ (ppm) 5.81-5.67 (1H, m), 5.11-5.08 (1H, m), 5.06-5.03 (1H, m), 2.28 (2H, dt, J=7.6 Hz, 1.2 Hz), 1.18 (6H, s), 0.63 (6H, s) $^{13}$C-NMR (CDCl$_3$, 75.6 MHz): δ (ppm) 177.0, 133.8, 118.2, 44.5, 43.2, 24.5, 2.5 MS (EI): m/z 222, 220 (M$^+$), 207, 205, 185, 95, 93, 83, 82, 55, 41

Example 4

Synthesis of 1,3-bis(2,2-dimethyl-4-pentenoyloxy)-1,1,3,3-tetramethyldisiloxane by Reaction of Allyl Methacrylate with 1,1,3,3-tetramethyldisiloxane A 100-ml four-necked flask equipped with a Dimroth reflux condenser, stirrer, thermometer and dropping funnel was purged with nitrogen. The flask was charged with 258 mg of Irganox 1330, 2.6 mg (0.005 mmol) of tris(pentafluorophenyl)borane, and 5 ml of toluene. While the contents were stirred, the flask was cooled in a water bath. A mixture of 63.1 g (0.50 mol) of allyl methacrylate and 33.6 g (0.50 mol) of 1,1,3,3-tetramethyldisiloxane was added dropwise over 9 hours from the dropping funnel while keeping an internal temperature of 1.5 to 12° C. The disappearance of 1,1,3,3-tetramethyldisiloxane was confirmed by GC. After the completion of dropwise addition, the contents were stirred at 2-4° C. for a further 3 hours. The resulting colorless clear reaction mixture was vacuum distilled, collecting 91.6 g of a colorless clear fraction having a boiling point of 101.5-103.5° C./0.2 kPa. On NMR and GC/MS analysis, the liquid was identified to be the target compound, 1,3-bis(2,2-dimethyl-4-pentenoyloxy)-1,1,3,3-tetramethyldisiloxane. The yield was 94.8%.

$^1$H-NMR (CDCl$_3$, 300 MHz): δ (ppm) 5.80-5.66 (2H, m), 5.08-5.05 (2H, m), 5.03-5.01 (2H, m), 2.26 (4H, dt, J=7.5 Hz, 1.1 Hz), 1.15 (12H, s), 0.29 (12H, s) $^{13}$C-NMR (CDCl$_3$, 75.6 MHz): δ (ppm) 177.3, 134.2, 117.9, 44.6, 43.0, 24.7, −0.5 MS (EI): m/z 386 (M$^+$), 371, 259, 133, 83, 55, 41

Example 5

Synthesis of 2,2-dimethyl-4-pentenoic Acid

A 100-ml four-necked flask equipped with a Dimroth reflux condenser, stirrer and thermometer was purged with nitrogen. The flask was charged with 17.7 g (0.0768 mol) of ethoxydimethylsilyl 2,2-dimethyl-4-pentenoate and 14.2 g (0.307 mol) of ethanol. The contents were stirred at room temperature for one hour, then at 60-65° C. for 5 hours. The reaction mixture was vacuum distilled, collecting 9.2 g of a colorless clear fraction having a boiling point of 78-79° C./0.6 kPa. On NMR and GC/MS analysis, the liquid was identified to be the target compound, 2,2-dimethyl-4-pentenoic acid. The yield was 93.4%. $^1$H-NMR (CDCl$_3$, 300 MHz): δ (ppm) 11.9 (1H, br), 5.84-5.70 (1H, m), 5.11-5.08 (1H, m), 5.07-5.04 (1H, m), 2.30 (2H, dt, J=7.3 Hz, 1.1 Hz), 1.19 (6H, s) $^{13}$C-NMR (CDCl$_3$, 75.6 MHz): δ (ppm) 184.6, 133.9, 118.2, 44.4, 42.2, 24.5 MS (EI): m/z 128 (M$^+$), 113, 83, 55, 41

Example 6

Synthesis of triethylsilyl 2,2-dimethyl-5-(triethoxysilyl)-pentanoate

A 100-ml four-necked flask equipped with a Dimroth reflux condenser, stirrer, thermometer and dropping funnel was purged with nitrogen. The flask was charged with 25 mg of BHT, 5.1 mg (0.01 mmol) of tris(pentafluorophenyl) borane, and 11.6 g (0.1 mol) of triethylsilane. The contents were stirred at room temperature for 0.5 hour, after which the flask was cooled at 10° C. in an ice water bath. 10.1 g (0.08 mol) of allyl methacrylate was added dropwise over 2 hours from the dropping funnel. The internal temperature rose to 18° C. at maximum. A 10% toluene solution of 1 mg (0.002 mmol) of tris(pentafluorophenyl)borane was added and 2.5 g (0.02 mol) of allyl methacrylate was added dropwise at 10-18° C. over 0.5 hour. After the completion of dropwise addition, the contents were stirred at 10° C. for a further 2 hours. GC analysis confirmed the disappearance of triethylsilane and the formation of triethylsilyl 2,2-dimethyl-4-pentenoate.

To the reaction mixture was added 32.5 mg (Pt 5 µmol) of a toluene solution (Pt 3 wt %) of platinum(0) tetramethyldivinyldisiloxane complex. With stirring, the internal temperature was adjusted to 60° C. using an oil bath. 16.4 g (0.10 mol) of triethoxysilane was added dropwise over 3.5 hours. The internal temperature rose to 70° C. at maximum.

After the completion of dropwise addition, the reaction mixture was heated at 70° C. and aged at the temperature for 6 hours. The conversion of triethoxysilane reached 99.5% or higher. The resulting pale yellow orange reaction mixture was vacuum distilled, collecting 33.1 g of a colorless clear fraction having a boiling point of 152-153° C./0.3 kPa. On NMR and GC/MS analysis, the liquid was identified to be the target compound, triethylsilyl 2,2-dimethyl-5-(triethoxysilyl)pentanoate. The yield was 81.4%.

$^1$H-NMR (CDCl$_3$, 300 MHz): δ (ppm) 3.78 (6H, q, J=7.0 Hz), 1.57-1.51 (2H, m), 1.43-1.30 (2H, m), 1.20 (9H, t, J=8.4 Hz), 1.13 (6H, s), 0.99-0.93 (9H, m), 0.78-0.69 (6H, m), 0.61-0.58 (2H, m) $^{13}$C-NMR (CDCl$_3$, 75.6 MHz): δ (ppm) 178.6, 58.3, 44.4, 43.3, 25.2, 18.4, 18.2, 11.1, 6.5, 4.5 $^{29}$Si—NMR (CDCl$_3$, 59.7 MHz): δ (ppm) 24.6, −45.4 MS (EI): m/z 406 (M$^+$), 377, 361, 360, 317, 303, 265, 257, 221, 202, 172, 163, 157, 119, 115, 87

Example 7

Synthesis of triethylsilyl 2,2-dimethyl-5-(dimethoxy-methylsilyl)pentanoate

A 100-ml four-necked flask equipped with a Dimroth reflux condenser, stirrer, thermometer and dropping funnel was purged with nitrogen. The flask was charged with 25 mg of BHT, 5.1 mg (0.01 mmol) of tris(pentafluorophenyl) borane, and 11.6 g (0.1 mol) of triethylsilane. The contents were stirred at room temperature for 0.5 hour, after which the flask was cooled at 21° C. in a water bath. 7.6 g (0.06 mol) of allyl methacrylate was added dropwise over 1.5 hours from the dropping funnel. The internal temperature rose to 28° C. at maximum. A 10% toluene solution of 1 mg (0.002 mmol) of tris(pentafluorophenyl)borane was added and 5.0 g (0.04 mol) of allyl methacrylate was added dropwise at 22-26° C. over 1 hour. After the completion of dropwise addition, the contents were stirred for a further 0.5 hour. GC analysis confirmed the disappearance of triethylsilane and the formation of triethylsilyl 2,2-dimethyl-4-pentenoate.

To the reaction mixture was added 32.5 mg (Pt 5 μmol) of a toluene solution (Pt 3 wt %) of platinum(0) tetramethyldivinyldisiloxane complex. With stirring, the internal temperature was adjusted to 46° C. using an oil bath. 10.6 g (0.10 mol) of dimethoxymethylsilane was added dropwise over 3.5 hours. The internal temperature rose to 58° C. at maximum. After the completion of dropwise addition, the reaction mixture was aged at 49-58° C. for 5 hours. The conversion of dimethoxymethylsilane reached 99.5% or higher. The resulting yellow reaction mixture was vacuum distilled, collecting 29.5 g of a colorless clear fraction having a boiling point of 129-130° C./0.2 kPa. On NMR and GC/MS analysis, the liquid was identified to be the target compound, triethylsilyl 2,2-dimethyl-5-(dimethoxymethylsilyl)pentanoate. The yield was 84.6%.

$^1$H-NMR (CDCl$_3$, 300 MHz): δ (ppm) 3.48 (6H, s), 1.56-1.51 (2H, m), 1.37-1.26 (2H, m), 1.13 (6H, s), 0.96 (9H, dt, J=0.9 Hz, 7.8 Hz), 0.74 (6H, dq, J=1.4 Hz, 7.8 Hz), 0.61-0.57 (2H, m), 0.08 (3H, s) $^{13}$C-NMR (CDCl$_3$, 75.6 MHz): δ (ppm) 178.3, 49.9, 44.4, 43.2, 25.1, 18.2, 13.6, 6.3, 4.4, −6.0 $^{29}$Si—NMR (CDCl$_3$, 59.7 MHz): δ (ppm) 24.6, −1.6 MS (EI): m/z 319 ([M-Et]$^+$), 259, 207, 202, 177, 172, 157, 115, 105, 87, 75, 59

Example 8

Synthesis of Triethylsilyl 2,2-dimethyl-5-(ethoxydimethyl-silyl)pentanoate

A 100-ml four-necked flask equipped with a Dimroth reflux condenser, stirrer, thermometer and dropping funnel was purged with nitrogen. The flask was charged with 220 mg of BHT, 5.1 mg (0.01 mmol) of tris(pentafluorophenyl) borane, and 11.6 g (0.1 mol) of triethylsilane. The contents were stirred at room temperature for 0.25 hour, after which the flask was heated at 40° C. in an oil bath. 8.8 g (0.07 mol) of allyl methacrylate was added dropwise over 1.5 hours from the dropping funnel. The heating was adjusted so as to maintain the internal temperature at 40-50° C. A 10% toluene solution of 2 mg (0.004 mmol) of tris(pentafluorophenyl)borane was added and 3.8 g (0.03 mol) of allyl methacrylate was added dropwise at 42-49° C. over 0.5 hour. After the completion of dropwise addition, the contents were stirred for a further 0.5 hour. GC analysis confirmed the disappearance of triethylsilane and the formation of triethylsilyl 2,2-dimethyl-4-pentenoate.

To the reaction mixture was added 32.5 mg (Pt 5 μmol) of a toluene solution (Pt 3 wt %) of platinum(0) tetramethyldivinyldisiloxane complex. With stirring, the internal temperature was adjusted to 52° C. using an oil bath. 5.2 g (0.05 mol) of ethoxydimethylsilane was added dropwise over 1 hour. The internal temperature rose to 58° C. at maximum. Again, 32.5 mg (Pt 5 μmol) of a toluene solution (Pt 3 wt %) of platinum(0) tetramethyldivinyldisiloxane complex was added, and 5.9 g (0.057 mol) of ethoxydimethylsilane was added dropwise over 2 hours. After the completion of dropwise addition, the reaction mixture was aged at 55-59° C. for 10 hours. The conversion of ethoxydimethylsilane reached 99.5% or higher. The resulting yellowish orange reaction mixture was vacuum distilled, collecting 29.3 g of a colorless clear fraction having a boiling point of 128-130.5° C./0.2 kPa. On NMR and GC/MS analysis, the liquid was identified to be the target compound, triethylsilyl 2,2-dimethyl-5-(ethoxydimethylsilyl)-pentanoate. The yield was 84.4% based on the triethylsilane.

$^1$H-NMR (CDCl$_3$, 300 MHz): δ (ppm) 3.63 (2H, q, J=7.0 Hz), 1.56-1.49 (2H, m), 1.34-1.21 (2H, m), 1.16 (3H, t, J=7.0 Hz), 1.14 (6H, s), 0.96 (9H, dt, J=0.9 Hz, 8.4 Hz), 0.74 (6H, dq, J=1.3 Hz, 8.2 Hz), 0.58-0.52 (2H, m), 0.07 (6H, s) $^{13}$C-NMR (CDCl$_3$, 75.6 MHz): δ (ppm) 178.4, 58.0, 44.7, 43.2, 25.1, 18.7, 18.4, 17.0, 6.4, 4.5, 2.2 $^{29}$Si—NMR (CDCl$_3$, 59.7 MHz): δ (ppm) 24.6, 16.7 MS (EI): m/z 346 (M$^+$), 317, 257, 219, 205, 202, 187, 172, 161, 157, 115, 103, 87, 75, 59

Example 9

Synthesis of 1,3-bis(4-carboxy-4-methylpentyl)-1,1,3,3-tetramethyldisiloxane via 2,2-dimethyl-4-(ethoxydimethyl-silyl)pentanoic Acid A 100-ml four-necked flask equipped with a Dimroth reflux condenser, stirrer, thermometer and dropping funnel was purged with nitrogen. The flask was charged with 17.3 g (50 mmol) of triethylsilyl 2,2-dimethyl-4-(ethoxydimethyl-silyl)pentanoate. With stirring at room temperature, 9.6 g (50 mmol) of a 28% methanol solution of sodium methoxide was added dropwise over 15 minutes. Stirring was continued for 1 hour. While the flask was slowly heated, the triethylmethoxysilane formed was removed by vacuum stripping. The disappearance of triethylsilyl 2,2-dimethyl-4-(ethoxydimethylsilyl)pantanoate was confirmed by GC. There was obtained 2,2-dimethyl-4-(ethoxydimethylsilyl)pentanoic acid in the sodium salt form. To this pale yellow solid residue, 10.1 g of 36% hydrochloric acid was added dropwise over 5 minutes. With stirring, the slurry mixture was heated under reflux at 97-102° C. for 4 hours. The mixture was cooled to room temperature and combined with 15 ml of ethyl acetate and 10 ml of water, followed by separation. The organic layer was washed with 10 ml of water, solvent stripped in vacuum, and dried, yielding 9.3 g of a white solid.

On NMR and MS analysis, the solid was identified to be the target compound, 1,3-bis(4-carboxy-4-methylpentyl)-1,1,3,3-tetramethyldisiloxane. The yield was 95.2%.

$^1$H-NMR (CDCl$_3$, 300 MHz): δ (ppm) 12.0 (2H, br), 1.58-1.53 (4H, m), 1.30-1.21 (4H, m), 1.17 (12H, s), 0.46-0.40 (4H, m), 0.02 (12H, s) $^{13}$C-NMR (CDCl$_3$, 75.6 MHz): δ (ppm) 185.2, 45.6, 42.2, 24.9, 18.8, 18.6, 0.3 $^{29}$Si—NMR (CDCl$_3$, 59.7 MHz): δ (ppm) 7.2 MS (EI): m/z 261, 245, 187, 149, 133 MS (CI isobutane): m/z 391 ([M+H]$^+$), 373, 261, 201, 187

Japanese Patent Application No. 2003-333014 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A process of preparing a γ,δ-unsaturated carboxylic acid silyl ester of the general formula (3), comprising the step of reacting an α,β-unsaturated carboxylic acid ester of the general formula (1) with a hydrosilane or hydrosiloxane of the general formula (2) in the presence of a catalytic amount of tris(pentafluorophenyl)borane,

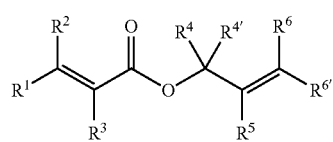

wherein $R^1$, $R^2$, $R^3$, $R^4$, $R^{4'}$, $R^5$, $R^6$ and $R^{6'}$ are each independently a monovalent $C_1$-$C_{20}$ hydrocarbon group which may be halo-substituted, a halogen atom, or a hydrogen atom, or a pair of $R^1$ and $R^2$, $R^1$ and $R^3$, $R^4$ and $R^{4'}$, $R^4$ and $R^6$, $R^{4'}$ and $R^6$, or $R^5$ and $R^{6'}$ may bond together to form a ring,

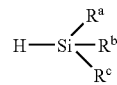

wherein $R^a$, $R^b$ and $R^c$ are each independently selected from the class consisting of $C_1$-$C_{20}$ alkyl, $C_6$-$C_{20}$ aryl, $C_7$-$C_{20}$ aralkyl, $C_1$-$C_{20}$ alkoxy, $C_6$-$C_{20}$ aryloxy, $C_7$-$C_{20}$ aralkyloxy, organosiloxy groups in which a group bonded to a silicon atom is a monovalent $C_1$-$C_{20}$ hydrocarbon group or hydrogen, substituted forms of the foregoing groups in which a hydrogen atom bonded to a carbon atom is substituted with a halogen atom, and halogen atoms, or a pair of $R^a$ and $R^b$, $R^a$ and $R^c$, or $R^b$ and $R^c$ may bond together to form a siloxane ring of 3 to 50 silicon atoms or a silicon-containing ring of 1 to 20 carbon atoms with the silicon atom to which they are bonded, or $R^a$, $R^b$ and $R^c$ may bond together to form a cage siloxane of 6 to 50 silicon atoms with the silicon atom to which they are bonded,

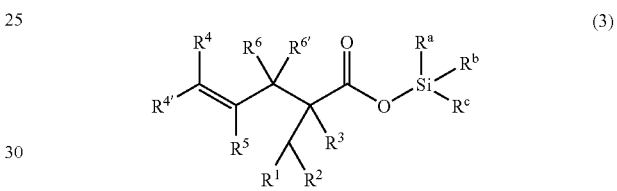

wherein $R^1$, $R^2$, $R^3$, $R^4$, $R^{4'}$, $R^5$, $R^6$, $R^{6'}$, $R^a$, $R^b$ and $R^c$ are as defined in formulae (1) and (2).

2. A process of preparing a γ,δ-unsaturated carboxylic acid of the general formula (4), comprising the step of desilylating the γ,δ-unsaturated carboxylic acid silyl ester of formula (3) resulting from the process of claim 1,

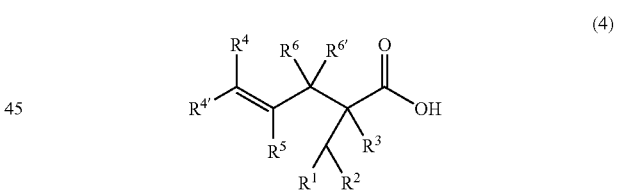

wherein $R^1$, $R^2$, $R^3$, $R^4$, $R^{4'}$, $R^5$, $R^6$, and $R^{6'}$ are as defined in claim 1.

3. An organosilicon compound having a silylated carboxyl group, represented by the general formula (5):

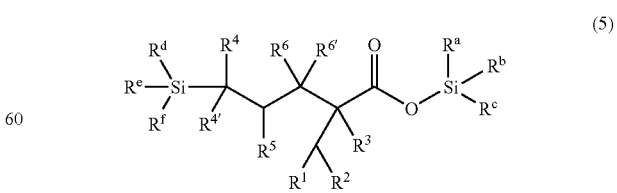

wherein $R^1$, $R^2$, $R^3$, $R^4$, $R^{4'}$, $R^5$, $R^6$ and $R^{6'}$ are each independently a monovalent $C_1$-$C_{20}$ hydrocarbon group which may be halo-substituted, a halogen atom, or a hydrogen atom, or a pair of $R^1$ and $R^2$, $R^1$ and $R^3$, $R^4$ and $R^{4'}$, $R^4$ and $R^6$, $R^{4'}$ and $R^6$, or $R^5$ and $R^{6'}$ may bond together to form a ring;

$R^a$, $R^b$ and $R^c$ are independently selected from the class consisting of $C_1$-$C_{20}$ alkyl, $C_6$-$C_{20}$ aryl, $C_7$-$C_{20}$ aralkyl, $C_1$-$C_{20}$ alkoxy, $C_6$-$C_{20}$ aryloxy, $C_7$-$C_{20}$ aralkyloxy, organosiloxy groups in which a group bonded to a silicon atom is a monovalent $C_1$-$C_{20}$ hydrocarbon group or hydrogen, substituted forms of the foregoing groups in which a hydrogen atom bonded to a carbon atom is substituted with a halogen atom, and halogen atoms, or a pair of $R^a$ and $R^b$, $R^a$ and $R^c$, or $R^b$ and $R^c$ may bond together to form a siloxane ring of 3 to 50 silicon atoms or a silicon-containing ring of 1 to 20 carbon atoms with the silicon atom to which they are bonded, or $R^a$, $R^b$ and $R^c$ may bond together to form a cage siloxane of 6 to 50 silicon atoms with the silicon atom to which they are bonded;

$R^d$ is selected from the class consisting of $C_1$-$C_{20}$ alkoxy, $C_6$-$C_{20}$ aryloxy, $C_7$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^e$ and $R^f$ are independently selected from the class consisting of $C_1$-$C_{20}$ alkyl, $C_6$-$C_{20}$ aryl, $C_7$-$C_{20}$ aralkyl, $C_1$-$C_{20}$ alkoxy, $C_6$-$C_{20}$ aryloxy, $C_7$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^d$, $R^e$ and $R^f$ may have a substituent group free of unsaturation that undergoes hydrosilylation, or a pair of $R^{d\ and\ Re}$, $R^d$ and $R^f$, or $R^e$ and $R^f$ may bond together to form a siloxane ring of 3 to 50 silicon atoms or a silicon-containing ring of 1 to 20 carbon atoms with the silicon atom to which they are bonded, or $R^d$, $R^e$ and $R^f$ may bond together to form a cage siloxane of 6 to 50 silicon atoms with the silicon atom to which they are bonded.

4. The organosilicon compound of claim 3, wherein in formula (5), $R^1$, $R^2$, $R^4$, $R^{4'}$, $R^5$, $R^6$, and $R^{6'}$ are hydrogen and $R^3$ is methyl.

5. A process of preparing an organosilicon compound having a silylated carboxyl group represented by the general formula (5), comprising the step of hydrosilylating the γ,δ-unsaturated carboxylic acid silyl ester of formula (3) resulting from the process of claim 1, using a hydrosilane or hydrosiloxane of the general formula (6),

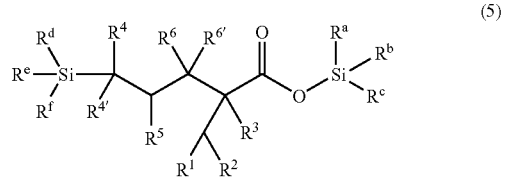

(5)

(6)

wherein $R^1$, $R^2$, $R^3$, $R^4$, $R^{4'}$, $R^5$, $R^6$, $R^{6'}$, $R^a$, $R^b$ and $R^c$ are as defined in claim 1, $R^d$ is selected from the class consisting of $C_1$-$C_{20}$ alkoxy, $C_6$-$C_{20}$ aryloxy, $C_7$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^e$ and $R^f$ are independently selected from the class consisting of $C_1$-$C_{20}$ alkyl, $C_6$-$C_{20}$ aryl, $C_7$-$C_{20}$ aralkyl, $C_1$-$C_{20}$ alkoxy, $C_6$-$C_{20}$ aryloxy, $C_7$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^d$, $R^e$ and $R^f$ may have a substituent group free of unsaturation that undergoes hydrosilylation, or a pair of $R^d$ and $R^e$, $R^d$ and $R^f$, or $R^e$ and $R^f$ may bond together to form a siloxane ring of 3 to 50 silicon atoms or a silicon-containing ring of 1 to 20 carbon atoms with the silicon atom to which they are bonded, or $R^d$, $R^e$ and $R^f$ may bond together to form a cage siloxane of 6 to 50 silicon atoms with the silicon atom to which they are bonded.

6. An organosilicon compound having a carboxyl group, represented by the general formula (7):

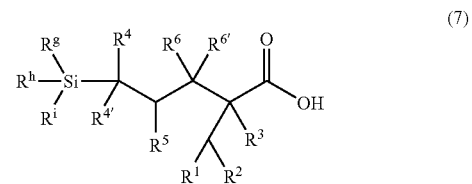

(7)

wherein $R^1$, $R^2$, $R^4$, $R^{4'}$, $R^5$, $R^6$ and $R^{6'}$ are hydrogen and $R^3$ is methyl;

$R^g$ is selected from the class consisting of hydroxyl, $C_1$-$C_{20}$ alkoxy, $C_6$-$C_{20}$ aryloxy, $C_7$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^h$ and $R^i$ are independently selected from the class consisting of hydroxyl, $C_1$-$C_{20}$ alkyl, $C_6$-$C_{20}$ aryl, $C_7$-$C_{20}$ aralkyl, $C_1$-$C_{20}$ alkoxy, $C_6$-$C_{20}$ aryloxy, $C_7$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^g$, $R^h$ and $R^i$ may have a substituent group free of unsaturation that undergoes hydrosilylation, or a pair of $R^g$ and $R^h$, $R^g$ and $R^i$, or $R^h$ and $R^i$ may bond together to form a siloxane ring of 3 to 50 silicon atoms or a silicon-containing ring of 1 to 20 carbon atoms with the silicon atom to which they are bonded, or $R^g$, $R^h$ and $R^i$ may bond together to form a cage siloxane of 6 to 50 silicon atoms with the silicon atom to which they are bonded.

7. A process of preparing an organosilicon compound having a carboxyl group represented by the general formula (7), comprising the step of desilylating an organosilicon compound having a silylated carboxyl group represented by the general formula (5),

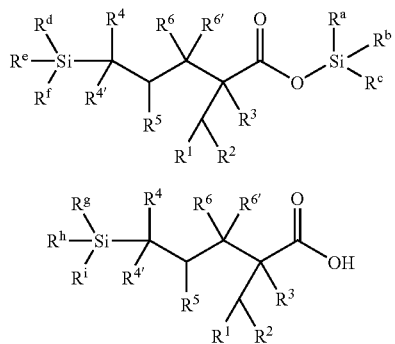

(5)

(7)

wherein $R^1$, $R^2$, $R^3$, $R^4$, $R^{4'}$, $R^5$, $R^6$ and $R^{6'}$ are each independently a monovalent $C_1$-$C_{20}$ hydrocarbon group which may be halo-substituted, a halogen atom, or a hydrogen atom, or a pair of $R^1$ and $R^2$, $R^1$ and $R^3$, $R^4$ and $R^{4'}$, $R^4$ and $R^6$, $R^{4'}$ and $R^6$, or $R^5$ and $R^{6'}$ may bond together to form a ring;

$R^a$, $R^b$ and $R^c$ are independently selected from the class consisting of $C_1$-$C_{20}$ alkyl, $C_6$-$C_{20}$ aryl, $C_7$-$C_{20}$ aralkyl, $C_1$-$C_{20}$ alkoxy, $C_6$-$C_{20}$ aryloxy, $C_7$-$C_{20}$ aralkyloxy, organosiloxy groups in which a group bonded to a silicon atom is a substituted or unsubstituted monovalent $C_1$-$C_{2-0}$ hydrocarbon group or hydrogen, substituted forms of the foregoing groups in which a hydrogen atom bonded to a carbon atom is substituted with a halogen atom, and halogen atoms, or a pair of $R^a$ and $R^b$, $R^a$ and $R^c$, or $R^b$ and $R^c$ may bond together to form a siloxane ring of 3 to 50 silicon atoms or a silicon-containing ring of 1 to 20 carbon atoms with the silicon atom to which they are bonded, or $R^a$, $R^b$ and $R^c$ may bond together to form a cage siloxane of 6 to 50 silicon atoms with the silicon atom to which they are bonded;

$R^d$ is selected from the class consisting of $C_1$-$C_{20}$ alkoxy, $C_6$-$C_{20}$ aryloxy, $C_7$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^e$ and $R^f$ are independently selected from the class consisting of $C_1$-$C_{20}$ alkyl, $C_6$-$C_{20}$ aryl, $C_7$-$C_{20}$ aralkyl, $C_1$-$C_{20}$ alkoxy, $C_6$-$C_{20}$ aryloxy, $C_7$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^d$, $R^e$ and $R^f$ may have a substituent group free of unsaturation that undergoes hydrosilylation, or a pair of $R^d$ and $R^e$, $R^d$ and $R^f$, or $R^e$ and $R^f$ may bond together to form a siloxane ring of 3 to 50 silicon atoms or a silicon-containing ring of 1 to 20 carbon atoms with the silicon atom to which they are bonded, or $R^d$, $R^e$ and $R^f$ may bond together to form a cage siloxane of 6 to 50 silicon atoms with the silicon atom to which they are bonded;

$R^g$ is selected from the class consisting of hydroxyl, $C_1$-$C_{20}$ alkoxy, $C_6$-$C_{20}$ aryloxy, $C_7$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^h$ and $R^i$ are independently selected from the class consisting of hydroxyl, $C_1$-$C_{20}$ alkyl, $C_6$-$C_{20}$ aryl, $C_7$-$C_{20}$ aralkyl, $C_1$-$C_{20}$ alkoxy, $C_6$-$C_{20}$ aryloxy, $C_7$-$C_{20}$ aralkyloxy, organosiloxy groups of 1 to 1,000 silicon atoms in which a group bonded to a silicon atom is a substituted or unsubstituted monovalent $C_1$-$C_{20}$ hydrocarbon group or hydrogen, and halogen atoms, $R^g$, $R^h$ and $R^i$ may have a substituent group free of unsaturation that undergoes hydrosilylation, or a pair of $R^g$ and $R^h$, $R^g$ and $R^i$, or $R^h$ and $R^i$ may bond together to form a siloxane ring of 3 to 50 silicon atoms or a silicon-containing ring of 1 to 20 carbon atoms with the silicon atom to which they are bonded, or $R^g$, $R^h$ and $R^i$ may bond together to form a cage siloxane of 6 to 50 silicon atoms with the silicon atom to which they are bonded.

* * * * *